United States Patent [19]

Chou

[11] Patent Number: 5,141,849
[45] Date of Patent: Aug. 25, 1992

[54] MARKER FOR EARLY DETECTION OF HUMAN HYDATIDIFORM MOLES AND CHORIOCARCINOMAS

[75] Inventor: Janice Chou, Potomac, Md.

[73] Assignee: The United States of America as represented by the Department of Health and Human Services, Washington, D.C.

[21] Appl. No.: 536,101

[22] Filed: Jun. 8, 1990

[51] Int. Cl.$^5$ ............ C12Q 1/68; G01N 33/53; A61K 37/02; C07H 15/12
[52] U.S. Cl. ............ 435/6; 435/7.1; 435/810; 536/26; 536/27; 536/28; 536/29; 530/326; 530/328; 530/387.9; 530/388.2; 530/388.85; 530/389.1; 530/389.7; 935/77; 935/78; 436/501; 436/94
[58] Field of Search ............ 536/26, 27, 28; 435/6, 435/7.1, 7.23; 530/328, 326, 387; 935/77, 78

[56] References Cited

PUBLICATIONS

Leslie et al., Linkage of two human pregnancy-specific $\beta_1$-glycoprotein genes: One is associated with hydatidiform mole, Proc. Natl. Acac. Sci., vol. 87, pp. 5822–5826, Aug. 1990.

Zimmermann et al., cDNA Cloning Demonstrates the Expression of Pregnancy-Specific . . . , Biochemical and Biophysical Research communications, vol. 163, No. 3, Sep. 1989, pp. 1197–1209.

Watanabe et al.., J. Biol. Chem. 263(4): 2049–2054 (Feb. 5, 1988).

Primary Examiner—Margaret Moskowitz
Assistant Examiner—Stephanie W. Zitomer
Attorney, Agent, or Firm—Cushman Darby & Cushman

[57] ABSTRACT

The present invention relates to a DNA segment comprising linked pregnancy-specific beta$_1$-glycoprotein (PS$\beta$G) genes encoding PSGGA protein and PSGGB protein. The invention further relates to a probe (DNA, RNA or peptide probe) specific for PSGGB mRNA or protein expressed in human hydatidiform molar trophoblastic tissue and to a bioassay for the detection of gestational trophoblastic diseases. The PSGGB-specific probes of the present invention hybridized most strongly with RNA from molar trophoblastic tissue, suggesting that the PSGGB-like species may be the gene preferentially expressed in gestational trophoblastic diseases.

19 Claims, 6 Drawing Sheets

FIG. 1

```
                                                                                                            GAATTCGGGCTGACC    15
                                                                                                              EcoRI
CTGCCCATGAGCTTGAGAATTGCTCTGCCCTGCCCTGGGAAGAGGCTCAGCACAGAAAGAGGAAGGACACAGCCGTGCTCAGAGAGTTTCTGGATCCTAGGCTTATCTCCACAGAGGAACACAAG    150

CAGCAGACC ATG GGA ACC CTC TCA GCC CCT CCC TGC ACA CAG CGC ATC AAA TGG AAG GGG CTC CTG CTC ACA GCA TCA CTT TTA AAC TTC TGG AAC CTG CCC    254
          Met Gly Thr Leu Ser Ala Pro Pro Cys Thr Gln Arg Ile Lys Trp Lys Gly Leu Leu Leu Thr Ala Ser Leu Leu Asn Phe Trp Asn Leu Pro    31
          • N Domain ACC ACT GCC CAA GTC ACG ATT GAA GCC GAG CCA GAG CCA ACC AAA GTT TCC GAG GGG AAG GAT GTT CTT CTA CTT GTC CAC AAT CTT TTA AAC TTC ACC GGC TAC    356
Thr Thr Ala Gln Val Thr Ile Glu Ala Glu Pro Glu Pro Thr Lys Val Ser Glu Gly Lys Asp Val Leu Leu Leu Val His Asn Leu Pro Gln Asn Leu Thr Gly Tyr    65

ATC TGG TAC AAA ATG AGG GAC ATG AGG GAC CTC TAC CAT CAT GTA TAT GTA GAC TCA ATT ACA ATT ATA TAT GGG CCT GCA TAT AGT GGA CGA GAA    458
Ile Trp Tyr Lys Met Arg Asp Leu Tyr His His Val Tyr Val Asp Ser Ile Thr Ile Ile Tyr Gly Pro Ala Tyr Ser Gly Arg Glu    99

ACA GCA TAT TCC AAT GCA TCC TTC ACC TTG ATC CAG ACT CTG AAT GTC ACC TAC CGG GAG GAC ATC AAG GAG GAT GAT ATG AGG GAG ACC GTG AGC TTA    560
Thr Ala Tyr Ser Asn Ala Ser Leu Leu Ile Gln Asn Val Thr Leu Ile His Ile Ile Lys Gly Asp Asp Met Glu Thr Val Ala Val Ser Leu    133
                    • Ia Domain GTA ACT GGA CGT TTC ACC TTC CAC TTA CAC CTG GAG ACT CTC CAT AAG CCT TCC ATC CCC AGG GAG ACC ATG AGG GAG GCT GTG AGC TTA    662
Val Thr Gly Arg Phe Thr Phe His Leu His Leu Glu Thr Leu His Lys Pro Ser Ile Pro Arg Glu Thr Met Glu Arg Ala Val Ser Leu    167

ACC TGT GAC CCT GAG ACT CCA GAC GCA AGC TAC CTG TGG TGG ATG AAT GGT CAG AGC CTC CCT ATG ACT CAC AGC TTG AAG CTG TCC GAA ACC AAC AGG ACC    764
Thr Cys Asp Pro Glu Thr Pro Asp Ala Ser Tyr Leu Trp Trp Met Asn Gly Gln Ser Leu Pro Met Thr His Ser Leu Lys Leu Ser Glu Thr Asn Arg Thr    201

CTC TTT CTA TTG GGT GTC ACA AAG TAT ACT GCA GGA CCC TAT GAA TGT GAA ATA CGG AAC CCA GTG AGT GCC CGC AGT GAC CGC ACC CTG AAT CTC    866
Leu Phe Leu Leu Gly Val Thr Lys Tyr Thr Ala Gly Pro Tyr Glu Cys Glu Ile Arg Asn Pro Val Ser Ala Ser Arg Asp Ser Val Thr Leu Asn Leu    235
• 2a Domain CTC CCG AAG CTG CCC AAG CCC TAC ATC ACC ATC AAC AAC TTA AAC CCC AGG GAG AAT AAG GAT GTC TTA AAC TTC ACC TGT GAA CCT AAG AGT GAG AAC TAC    968
Leu Pro Lys Leu Pro Lys Pro Tyr Ile Thr Ile Asn Asn Leu Asn Pro Arg Glu Asn Lys Asp Val Leu Asn Phe Thr Cys Glu Pro Lys Ser Glu Asn Tyr    269
```

FIG. 1 (CON'T)

```
ACC TAC ATT TGG TGG CTA AAT GGT CAG AGC CTC CCG GTC AGT CCC ATT GAA AAC AGG ATC CTC ATT CTA CCC AGT GTC ACG AGA AAT      1070
Thr Tyr Ile Trp Trp Leu Asn Gly Gln Ser Leu Pro Val Ser Pro Ile Glu Asn Arg Ile Leu Ile Leu Pro Ser Val Thr Arg Asn       303
                                                                                       * b Domain
GAA ACA GGA CCC TAT CAA CCC TAT GAA TGT GAA ATA CGG GAC GTC CGC AGT GAC CCA GTC ACC CTG AAT GTC CTC TAT GGT CCA GAC CTC CCC AGA ATT  1172
Glu Thr Gly Pro Tyr Gln Pro Tyr Glu Cys Glu Ile Arg Asp Val Arg Ser Asp Pro Val Thr Leu Asn Val Leu Tyr Gly Pro Asp Leu Pro Arg Ile   337

TAC CCT TCA TTC TAC ACC TAT TAC CGT TCA GGA GAA GTC CTC TAC TTG TCC TCT GCG GAC TCT AAC CCA GCA CAG TAT TCT TGG ACA ATT AAT GAA AAG  1274
Tyr Pro Ser Phe Tyr Thr Tyr Tyr Arg Ser Gly Glu Val Leu Tyr Leu Ser Ser Ala Asp Ser Asn Pro Ala Gln Tyr Ser Trp Thr Ile Asn Glu Lys   371

TTT CAG CTA CCA GGA CAA AAG CTC TTT ATC CGC CAT ATT ACT ACA AAG CAT AGC CTC TGT CTT GTT TGC TCT CGT AAC TCA GCC ACT GGC AAG GAA AGC  1376
Phe Gln Leu Pro Gly Gln Lys Leu Phe Ile Arg His Ile Thr Thr Lys His Ser Leu Cys Leu Val Cys Ser Val Arg Asn Ser Ala Thr Gly Lys Glu Ser  405

TCC AAA TCC ATG ACA GTC GAA GTC TCT GGT AAG TCG TTG GCA ATA GGG TTT TAGGTGGAGTCTATCTGACATTGGCATTCAGAGAAGAGTCAGGAAAACAATTGTATT   1490
Ser Lys Ser Met Thr Val Glu Val Ser Gly Lys Ser Trp Ile Pro Ala Ser Leu Ala Ile Gly Phe End                                           426

CCCAGCCTGTCCCATGGGCACAAGCAAATCCCAAATTCTCCTGAACCCTCCAAATTGTCTAAGAACTTCGAAACTTGAAAACTTCTAAGAACAACAGGCTGATATCTTCATAATATTCCCAGCCTGATCTCATAATATTCCCAGCCTAGACCAAGCAGGAA  1625

GAACATTGATTCATTGAATAAACTATACTTCTGGGAACCGTAATTGAAACATTTACTTTTGCTTTCTACCTGACTGCCCAGAATTGGGCAACTATTCATGAGAATTGATATGTTATGGTAATACACATATTTGCACA  1760

TTATAGCAGTTCAATAAACTATACTTCTGGGAACCGTAATTGAAACATTTACTTTTGCTTTCTACCTGACTGCCCAGAATTGGGCAACTATTCATGAGAATTGATATGTTATGGTAATACACATATTTGCACA  1895
                                                                              G
AGTAACAGTAACAATCTGCTTCTTTGTAACATGACACATTTGAAATCATTGGTTATATTAAAAACATGAATGAACCAATATGAACTGCAGGCAAAGTC  2030

TGAAGTCAGGCCTTGGTTTGGCTTCCTATTCTCAAGAGGTTTGTGAAGATTTAATCTCAGATTCCTTATAAAAACTTAGAAGACAGCCTACATGGTCCATTGCTACTCTTGCTCTGCACTT   2165

ATGTAAACAATCAGACCACCATTTGAAGAAACTCCACCTATTTTGCAAACAAACTTATTCTACTGAAATTATCATTGGTAAAAGTAGAGATGCCCATAGAGGGAAAAATTATGTGGAAAATAAAAACTGTAGTATA  2300

CCTGTGTACCCGAATTC                                                                                                                      2315
         EcoRi
```

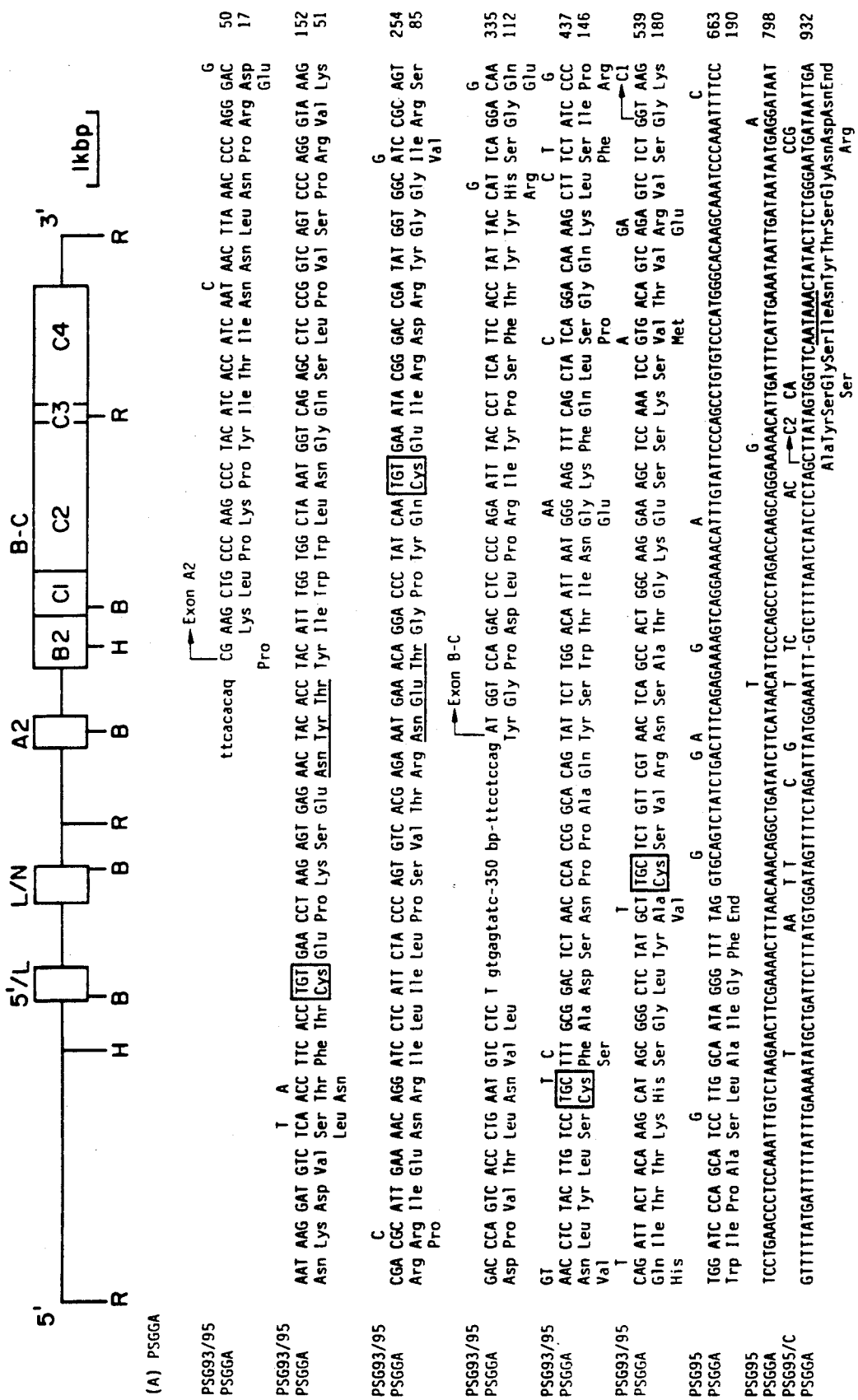

FIG. 2(CON'T-1)

FIG. 2 (CONT-2)

MARKER FOR EARLY DETECTION OF HUMAN HYDATIDIFORM MOLES AND CHORIOCARCINOMAS

BACKGROUND OF THE INVENTION

In general, the present invention relates to pregnancy-specific beta$_1$-glycoproteins. The present invention relates, in particular, to pregnancy-specific beta$_1$-glycoprotein mRNA that is preferentially expressed in human hydatidiform molar trophoblastic tissue.

Pregnancy-specific beta$_1$-glycoprotein (PS$\beta$G) was the first of a group of pregnancy associated proteins identified (for reviews see Tatarinov, Y. S., 1978, *Gynecol. Obstet. Invest.* 9:65-97; and Sorensen, S., 1984, *Tumor Biol.* 5:275-302). It is detectable in maternal serum as early as 18 days after ovulation (Tatarinov, Y. S. and Masyukevich, V. N., 1970, *Byull. Eksp. Biol. Med. USSR* 69:66-68). Maternal serum concentrations reach 200-400 µg/ml by the third trimester, making PS$\beta$G a major secretory product of the human placenta (Tatarinov, Y. S. and Masyukevich, V. N., 1970, *Byull. Eksp. Biol. Med. USSR* 69:66-68; Lin, T. M., Halbert, S. P. and Spellacy, W. N., 1974, *J. Clin. Invest.* 54:576-582). PS$\beta$G has been used clinically to diagnose pregnancy and to predict some pregnancy-related complications. For example, low PS$\beta$G values are associated with poor pregnancy outcome in threatened abortions (Wurz, H., Geiger, W., Kunzig, H. J., Jabs-Lehmann, A., Bohn, H. and Luben, G., 1981, *J. Perinat. Med.* 2:67-78; Hertz, J. B. and Schultz-Larsen, P., 1983, *Int. J. Gynaecol. Obstet.* 21:111-117; Masson, G. M., Anthony, F. and Wilson, M. S., 1983, *Br. J. Obstet. Gynaecol.* 90:146-149), intrauterine growth retardation (Tamsen, L., Johansson, S. G. O. and Axelsson, O., 1983, *J. Perinat. Med.* 11:19-25), fetal hypoxia (MacDonald, D. J., Scott, J. M., Gemmel, R. S. and Mack, D. S., 1983, *Am. J. Obstet. Gynecol.* 147:430-436), and preeclampsia (Grudzinskas, J. G., Gordon, Y. B., Menabawey, M., Lee, J. N., Wadsworth, J. and Chard, T., 1983, *Am. J. Obstet. Gynecol.* 147:10-12). The clinical uses of PS$\beta$G are not limited to pregnancy; it is found in the sera of most patients with hydatidiform mole, invasive mole, and choriocarcinoma (a treatable cancer with excellent prognosis) (Tatarinov, Y. S., 1978, *Gynecol. Obstet. Invest.* 9:65-97; Lin, T. M., Halbert, S. P. and Spellacy, W. N., 1974, *J. Clin. Invest.* 54:576-582), and it has been employed as a marker for monitoring the treatment of choriocarcinoma (Tatarinov, Y. S., 1978, *Gynecol. Obstet. Invest.* 9:65-97).

Although PS$\beta$G has been used as a diagnostic marker, the present assays for PS$\beta$G suffer from several shortcomings which limit their utility for such diagnostic purposes. First, the presently known PS$\beta$G marker is a normal placental protein which is produced at variably high levels during pregnancy and thus is not specific for hydatidiform moles or choriocarcinomas, and elevated levels of this protein do not occur in the sera of all patients with these pathologic conditions. Thus there is a need for compositions and methods for more specific and reliable detection of human gestational trophoblastic diseases including hydatidiform moles and choriocarcinomas. The biological function of PS$\beta$G is unknown. In order to more completely understand this potentially important protein and its function in pregnancy, the present inventor has undertaken a number of studies to characterize human PS$\beta$G. Thus, it was found that placental PS$\beta$G represents a family of closely related glycoproteins of 72, 64, and 54 kDa, and that placental poly(A)$^-$ RNA directed the synthesis of three polypeptides of 50, 48 (major), and 36 kDa as immunoprecipitated by anti-PS$\beta$G serum (Watanabe, S. and Chou, J. Y., 1988, *J. Biol. Chem.* 263:2049-2054). Moreover, near-full length cDNAs encoding members of the PS$\beta$G family were recently isolated and characterized in the laboratory of the present inventor (Watanabe, S. and Chou, J. Y., 1988, *J. Biol. Chem.* 263:2049-2054; Watanabe, S. and Chou, J. Y., 1988, in *Placental and Endometrial Proteins*, ed. Mizutani, S., VNU Science Press, Japan, pp. 155-158) as well as by others (Streydio, C., Lacka, K., Swillens, S. and Vassart, G., 1988, *Biochem. Biophys. Res. Commun.* 154:130-137; Rooney, B. C., Horne, C. H. W. and Hardman, N., 1988, *Gene* 71:439-449; Chan, W. Y., Borjigin, J., Zheng, Q.-X. and Shupert, W. L., 1988, *DNA* 7:545-555; Khan, W. N., Osterman, A. and Hammarstrom, S., 1989, *Proc. Natl. Acad. Sci. U.S.A.* 86:3332-3336; Khan, W. N. and Hammarstrom, S., 1989, *Biochem. Biophys. Res. Commun.* 161:525-535; McLenachan, T. and Mansfield, B., 1989, *Biochem. Biophys. Res. Commun.* 162:1486-1493; Zimmermann, W., Weiss, M. and Thompson, J. A., 1989, *Biochem. Biophys. Res. Commun.* 163:1197-1209; Niemann, S. C., Flake, A., Bohn, H. and Bartels, I., 1989, *Hum. Genet.* 82:239-243). Recently, two gene fragments which share strong sequence similarity with the reported PS$\beta$G cDNAs have been reported (Oikawa, S., Inuzuka, C., Kosaki, G. and Nakazato, H., 1988, *Biochem. Biophys. Res. Commun.* 156:68-77; Oikawa, S., Inuzuka, C., Kuroki, M., Matsuoka, Y., Kosaki, G. and Nakazato, H., 1989, *Biochem. Biophys. Res. Commun.* 163:1021-1031).

A careful analysis of the structure of PS$\beta$G has led to the discovery that it is closely related to the carcinoembryonic antigen (CEA) family (Oikawa, S., Nakazato, H. and Kosaki, G., 1987, *Biochem. Biophys. Res. Commun.* 142, 511-518; Beauchemin, N., Benchimol, S., Cournoyer, D., Furks, A. and Stanners, C. P., 1987, *Mol. Cell Bio.* 7, 3221-3230). CEA has recently been shown to be an intercellular adhesion molecule mediating aggregation of cultured human colon adenocarcinoma cells (Benchimol, S., Furks, A., Jothy, S., Beauchemin, N., Shirota, K. and Stanners, C. P., 1989, *Cell* 57, 327-334). Both PS$\beta$G and CEA are members of the immunoglobulin superfamily (Streydio, C., Lacka, K., Swillens, S. and Vassart, G., 1988, *Biochem. Biophys. Res. Commun.* 154, 130-137; Rooney, B. C., Horne, C. H. W. and Hardman, N., 1988, *Gene* 71, 439-449; Chan, W.-Y., Borjigin, J., Zheng, Q.-X. and Shupert, W. L., 1988, *DNA* 7, 545-555; Oikawa, S., Nakazato, H., and Kosaki, G., 1987, *Biochem. Biophys. Res. Commun.* 142, 511-518; Beauchemin, N., Benchimol, S., Cournoyer, D., Furks, A. and Stanners, C. P., 1987, *Mol. Cell Bio.* 7, 3221-3230; Watanabe, S. and Chou, J. Y., 1988, *Biochem. Biophys. Res. Commun.* 152, 762-768) which includes proteins that are arranged in domains and have constant and variable regions. A group of proteins including neural cellular-adhesion molecule (N-CAM) (for a review see Cunningham, B. A., Hemperly, J. J., Murray, B. A., Predoger, E. A., Brackenbury, R. and Edelman, G. M., 1987, *Science* 236, 799-806) within the immunoglobulin superfamily contain the surface active tripeptide Arg-Gly-Asp which acts in cell-surface recognition. Many members of the PS$\beta$G gene family (including PSGGB in this study) are closely related to N-CAM and encode proteins which contain the Arg-Gly-Asp tripeptide (Streydio, C., Lacka, K., Swillens, S. and Vassart, G., 1988, Biochem. Biophys. Res. Commun. 154, 130-137; Rooney, B. C., Horne, C. H. W. and Hardman, N., 1988, Gene 71, 439-449; Khan, W. N. and Hammarstrom, S., 1989, Biochem. Biophys. Res. Commun. 161, 525-535; Zimmermann, W., Weiss, M. and Thompson, J. A., 1989, Biochem. Biophys. Res. Commun. 163, 1197-1209; Oikawa, S., Inuzuka, C., Kuroki, M., Matsuoka, Y., Kosaki, G. and Nakazato, H., 1989, Biochem. Biophys. Res. Commun. 163 1021-1031). Further, the PSGGB-encoded protein may be involved in the genesis of gestational trophoblastic disease by acting as adhesion molecule. This hypothesis is supported by data demonstrating that PSGGB-like mRNA is preferentially expressed in molar trophoblastic tissue. The PSGGB-like product may also serve as a more specific marker for molar pregnancy.

SUMMARY OF THE INVENTION

It is an object of the present invention to provide a means of early diagnosis of gestational trophoblastic diseases such as hydatidiform moles and choriocarcinomas.

It is a further object of the present invention to provide DNA or RNA probes and immunological reagents which are specific for certain PS$\beta$G mRNAs and polypeptide species preferentially expressed in gestational trophoblastic disease including hydatidiform moles and choriocarcinomas.

Various other objects and advantages of the present invention will become apparent from the drawings and the following description of the present invention.

In one embodiment, the present invention relates to a DNA segment comprising linked pregnancy-specific beta$_1$-glycoprotein (PS$\beta$G) genes encoding a PSGGA protein and a PSGGB protein.

In another embodiment, the present invention relates to a DNA or RNA probe consisting essentially of the following nucleotide sequence: the sense strands 5'-CACGGTCAAATTATATATGGGCCTGCCTAC-3' and/or 5'-GAGACAGCATCTCCCCAGGT-TACCTATGCTGGTCCAAACACCTGGTTTC AAGAAATCCTTCTGCTG-3' and/or the antisense strands 5'-GTAGGCAGGCCCATATATAATTT-GACCGTG-3'and/or 5'-CAGCAGAAG-GATTTCTTGAAACCAGGTGTTTGGACCAG-CATAGGTAACC TGGGGAGATGCTGTCTC-3'.

In another embodiment, the present invention relates to a peptide encoded in the sense sequence given above and having the following amino acid sequence: N terminus-His Gly Gln Ile Ile Tyr Gly Pro Ala Tyr-C terminus and/or N terminus-Glu Thr Ala Ser Pro Gln Val Thr Tyr Ala Gly Pro Asn Thr Trp Phe Gln Glu Ile Leu Leu Leu-C terminus.

In a further embodiment, the present invention relates to an antibody specific for all, or a unique portion of the polypeptide encoded by the PSGGB pregnancy-specific beta$_1$-glycoprotein mRNA that is preferentially expressed in human hydatidiform molar trophoblastic tissue.

In yet another embodiment, the present invention relates to a bioassay for detection of a gestational trophoblastic disease comprising the steps of:
i) contacting a tissue sample with a probe specific for PSGGB mRNA expressed in human hydatidiform molar trophoblastic tissue, under conditions such that regions of messenger RNA (mRNA) in the tissue sample and the probe with complementary sequences will base pair so that a RNA:probe complex is formed; and
ii) detecting the presence or absence of the complex.

In a further embodiment, the present invention relates to a bioassay for detection of a gestational trophoblastic disease comprising the steps of:
i) contacting a tissue sample with the antibody specific for all, or a unique portion of the polypeptide encoded by the PSGGB pregnancy-specific beta$_1$-glycoprotein mRNA that is preferentially expressed in human hydatidiform molar trophoblastic tissue under conditions such the antibody can form a complex with the polypeptide encoded by the PSGGB pregnancy-specific beta$_1$-glycoprotein mRNA in the tissue sample; and
ii) detecting the presence or absence of the antibody:-polypeptide complex.

In another embodiment, the present invention relates to a diagnostic kit comprising a probe specific for PSGGB and reagents to effect formation of and detection of RNA:DNA or RNA:RNA complex.

In another embodiment, the present invention relates to a immunodetection kit comprising antibodies specific all, or a unique portion of the polypeptide encoded in PSGGB and reagents to effect formation of and detection of polypeptide:antibody or peptide:antibody complex.

BRIEF DESCRIPTION OF THE FIGURES

FIG. 1. shows the nucleotide and deduced amino acid sequences of a novel PS$\beta$G cDNA of the present invention, PSG95. The 5'-sequence of a previously known PS$\beta$G cDNA, PSGC (Streydio, C., Lacka, K., Swillens, S. and Vassart, G., 1988, Biochem. Biophys. Res. Commun. 154:130-137), begins at nucleotide 45 (indicated as #) of PSG95. Arrowheads indicate the leader (L) peptide and the N, A1, A2, B2 protein domains of the PSG95 encoded protein. Sites of potential asparagine-linked glycosylation and poly (A) addition are underlined and the asterisks indicate the cysteine residues involved in disulfide bridge formation. The potential termination codon (TGA) for PSGC is boxed, and the shaded area represents the sequence which is present in the cDNA of the present invention but absent from PSGC.

Figure 2:
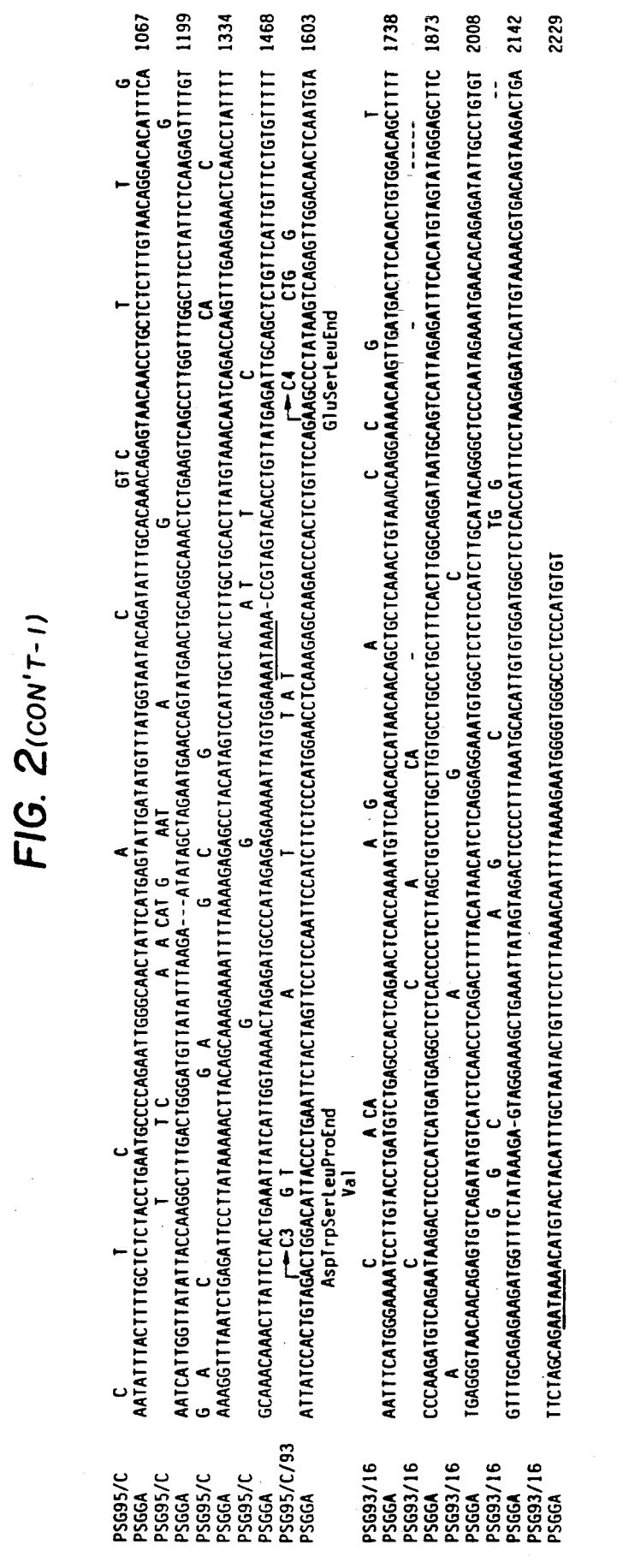
Figure 2:
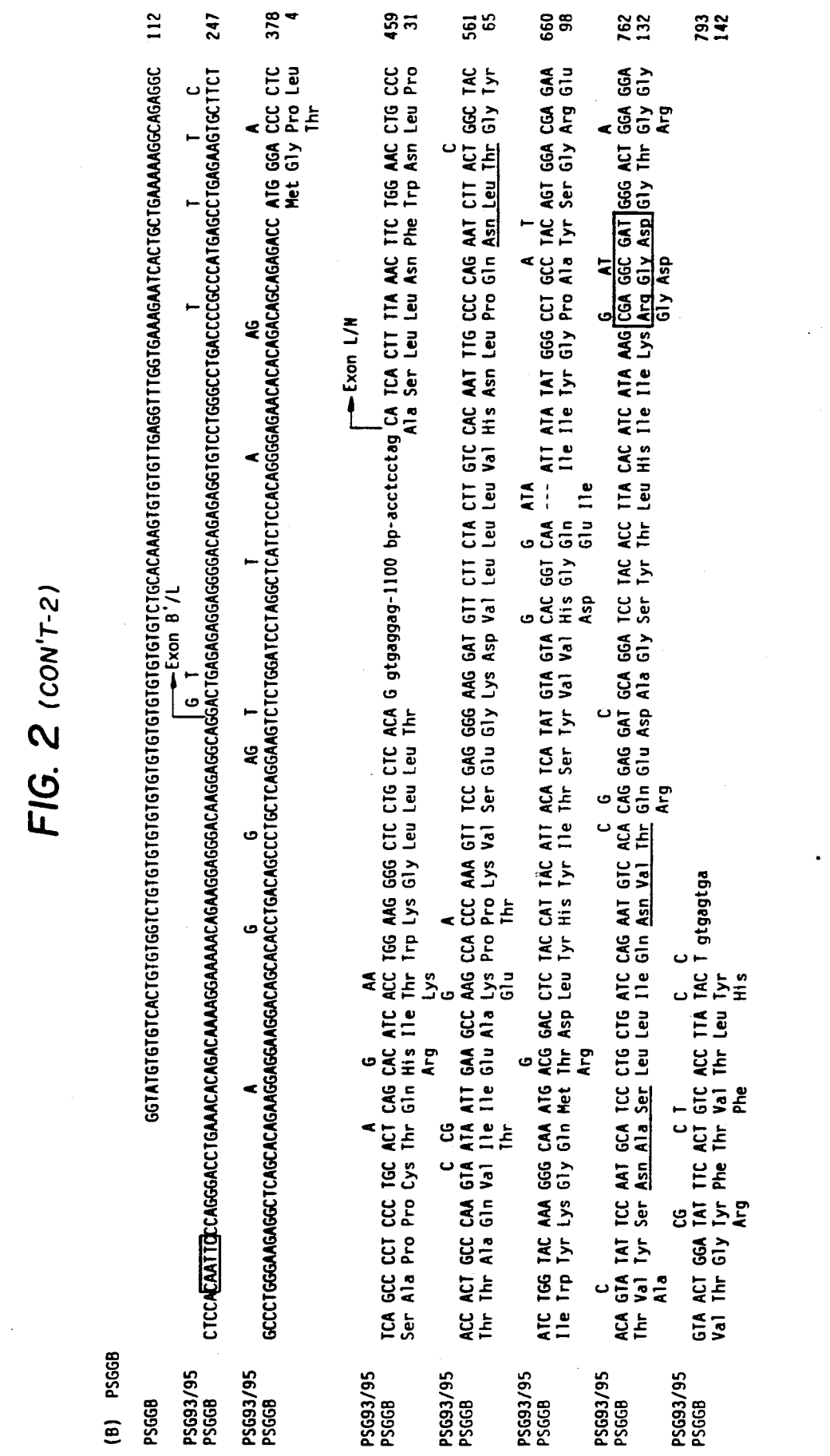

FIG. 2. depicts a restriction map and the nucleotide and deduced amino acid sequences of two linked PS$\beta$G genes, PSGGA and PSGGB, as compared to cDNAs PSG16, PSG93, PSG95 and PSGC. (A) The upstream gene, PSGGA, contains the A2 and B-C exons. The B-C exon contains four alternative splicing sites (C1, C2, C3, and C4) which may be involved in the generation of four PS$\beta$G mRNAs, each encoding a protein with a different carboxyl terminus. The PSG95-like 3'-sequence is composed of C1 and C2, the PSGC-like 3'-sequence is composed of C2, the PSG93-like 3'-sequence is composed of C3 and C4, and the PSG16-like 3'-sequence is composed of C4. The cysteine residues are boxed and the potential asparagine-linked glycosylation sites and the poly(A) addition sequences are underlined. (B) The downstream gene, PSGGB, contains the 5'/L and L/N exons. The CAAT box and Arg-Gly-Asp tripeptide are boxed.

DESCRIPTION OF SPECIFIC EMBODIMENTS

Figure 3:
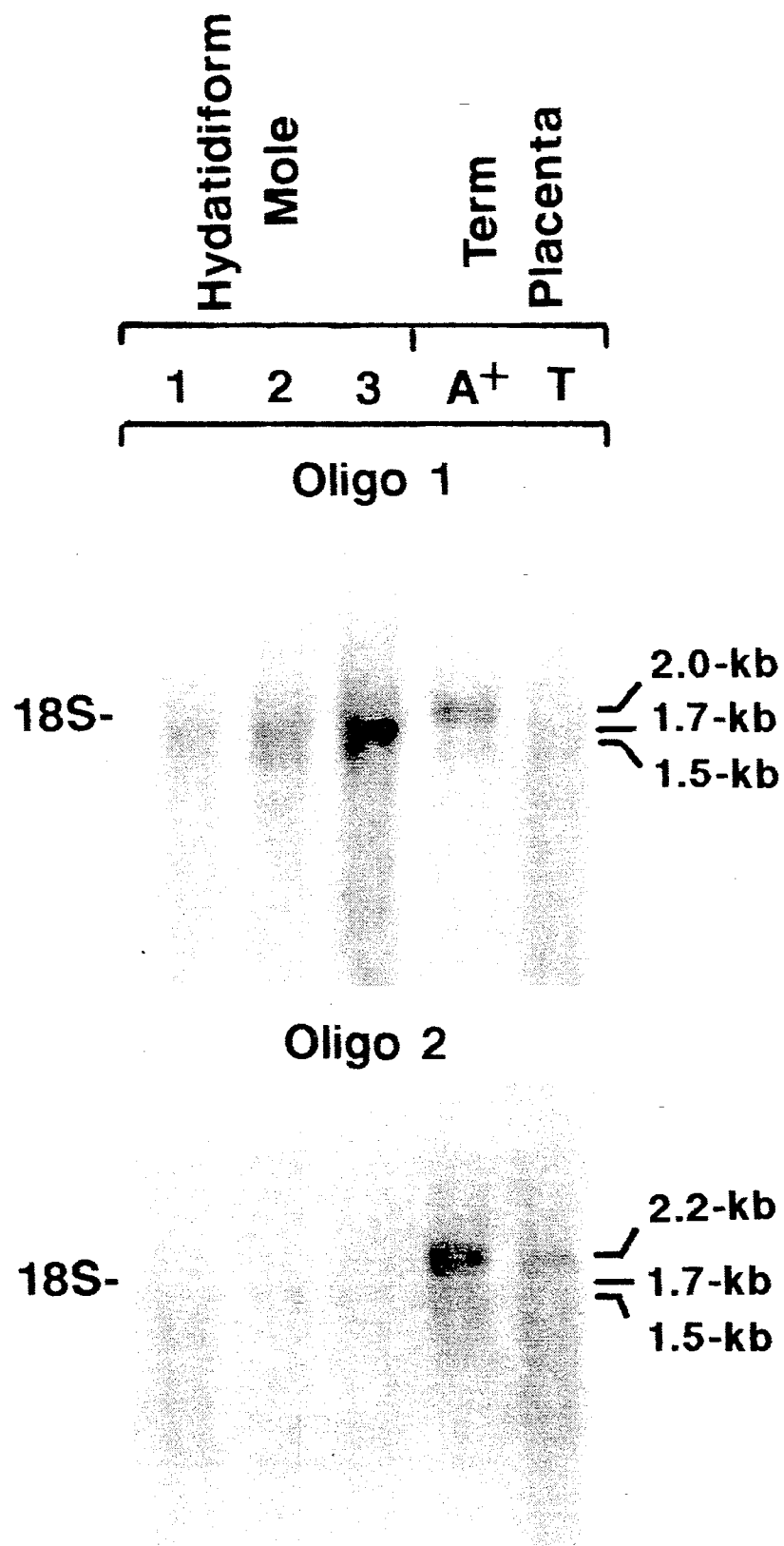
FIG. 3. shows Northern-blot hybridization of placental and hydatidiform mole RNAs with PSGGA and PSGGB specific probes. Total (20 $\mu$g/lane, T) or poly(A)$^+$ (2 $\mu$g/lane, A$^+$) RNAs from human term placenta and hydatidiform moles were separated by electrophoresis on formaldehyde-agarose gels. RNA was hybridized to $^{32}$P-labeled oligonucleotide probes containing nucleotides 619-648 (oligo 1) of PSGGB or nucleotides 45-68 (oligo 2) of PSGGA. Samples 1 and 2 are total RNAs from two non-invasive moles, and sample 3 is total RNA from an invasive mole.

The present invention relates to the isolation and characterization of a DNA segment comprising two linked PS$\beta$G genes which encode the PSGGA and the PSGGB proteins, members of the PS$\beta$G protein family. PS$\beta$G is a family of proteins with many closely related individual members encoded by more than one gene that are located on chromosome 19 (Barnett, T. R., Pickle, W., Rae, P. M., Hart, J., Kamarck, M. and Elting, J., 1989, *Am. J. Hum. Genet.* 44, 890-893; Lei, K. J., and Chou, J. Y., unpublished results). In addition to this genomic clone, the present inventor has identified another clone containing two different linked PS$\beta$G genes. Taken together, the results indicate that all of PS$\beta$G genes may be linked.

The present invention further relates to a bioassay for detection of a gestational trophoblastic disease comprising the steps of:

i) contacting a tissue sample, such as, the suitable tissue samples listed below, with a probe (such as a DNA probe or an RNA probe) specific for PSGGB mRNA expressed in human hydatidiform molar trophoblastic tissue, under conditions such that regions of messenger RNA (mRNA) in the tissue sample and the probe with complementary sequences will base pair so that a RNA:probe complex is formed; and ii) detecting the presence or absence of the complex.

Suitable tissue samples for use in the present invention include, for example, tumor biopsies, placental and endometrium and myometrium tissues, fetal tissues, fetal sera, maternal sera, amnion tissues and amniotic fluids. Gestational trophoblastic diseases to which the present invention relates include, but are not limited to, hydatidiform moles, invasive moles and choriocarcinomas, preferably, hydatidiform moles.

Advantageously, the probe to which the present invention relates is specific for the PSGGB mRNA that is preferentially expressed in human hydatidiform molar trophoblastic tissue. In other words, this probe is not sufficiently complementary to other 1.7-kilobase mRNA species for pregnancy-specific beta$_1$-glycoprotein that may be expressed in normal trophoblastic tissues, for instance, to allow detection of these other 1.7 kb mRNA species under hybridization conditions where the mRNA species that is preferentially expressed in human hydatidiform molar trophoblastic tissue is detectable.

The probe to which the invention relates may be a DNA or RNA molecule, either single-stranded or double-stranded, comprising nucleotides found in natural nucleic acids or chemically modified nucleotides which are able to form specific base pairs of the same specificity as one of the natural DNA or RNA nucleotides. In a presently preferred embodiment of this method, the probe is a single-stranded DNA oligonucleotide having the following sequence: the sense strands 5'-CACGGT-CAAATTATATATGGGCCTGCCTAC-3'and/or 5'-GAGACAGCATCTCCCCAGGTTACC-TATGCTGGTCCAAACACCTGGTTTC AA-GAAATCCTTCTGCTG-3' and/or the antisense strands 5'-GTAGGCAGGCCCATATATAATTT-GACCGTG-3'and/or 5'-CAGCAGAAG-GATTTCTTGAAACCAGGTGTTTGGACCAG-CATAGGTAACC TGGGGAGATGCTGTCTC-3'. As one skilled in the art will appreciate, probes derived from the sense strand can be used to detect cDNA and genomic clones containing these sequences, while probes derived from the antisense strand can be used to detect mRNA species.

The present invention also relates to a peptide encoded in the above-identified sense sequences. The peptide has the following amino acid sequence: N terminus-His Gly Gln Ile Ile Tyr Gly Pro Ala Tyr-C terminus and/or N terminus-Glu Thr Ala Ser Pro Gln Val Thr Tyr Ala Gly Pro Asn Thr Trp Phe Gln Glu Ile Leu Leu Leu-C terminus. The peptide of the present invention can be used to generate antibodies specific for all, or a unique portion, of the polypeptide encoded by PSGGB.

Moreover, in another aspect, the present invention relates to an antibody specific for the polypeptide encoded by all, or a unique portion of the PSGGB pregnancy-specific beta$_1$-glycoprotein mRNA that is preferentially expressed in human hydatidiform molar trophoblastic tissue. A "unique portion" as used herein consists of at least 5 (or 6) amino acids or correspondingly, 15 (or 18) nucleotides, for example, the polypeptides encoded by the above-described probes.

The antibodies of the present invention are made, for example, against a polypeptide or peptide encoded by the mRNA using standard methodologies well known in the art of experimental immunology. The polypeptide or peptide can be isolated from a natural source, produced recombinantly or chemically synthesized. These antibodies include, for example: monoclonal antibodies raised in mice against intact, purified protein from human tissues or serum, or produced by recombinant DNA methods; or monospecific antibodies produced according to methods described by the following two references: "Cloning of the immunological repertoire in *E. coli* for generation of monoclonal catalytic antibodies: Construction of a heavy chain variable region-specific cDNA library". Proc. Natl. Acad. Sci. 86:5728-5722, 1989 and "Generation of a large combinatorial library of the immunoglobin reprtoire in phage lamba:. Science 246: 1275-1281, 1989; and polyclonal antibodies raised in rabbits against synthetic peptides with sequences based on amino acid sequences predicted from the cDNA sequence.

Advantageously, the antibody of this invention is selected to bind specifically to the polypeptide encoded by the PSGGB pregnancy-specific beta$_1$-glycoprotein mRNA that is preferentially expressed in human hydatidiform molar trophoblastic tissue and not to other species of pregnancy-specific beta$_1$-glycoprotein. Preferably, this antibody binds specifically to this protein species when this PS$\beta$G protein is in its native (biologically active) conformation or denatured conformation. This preferred antibody of this invention is used, for example, in a method for specific detection of the polypeptide product preferentially expressed in human hydatidiform molar trophoblastic tissue. Thus, this method of this invention can be used diagnostically for detection of this species of PS$\beta$G in blood or other human specimens which results from expression of this protein in human hydatidiform molar trophoblastic tissue.

The present invention also relates to a diagnostic kit comprising a DNA or RNA probe of the present invention specific for PSGGB and reagents to effect formation of and detection of RNA:DNA complex or RNA:RNA complex. Suitable reagents for use in the diagnostic kit include, but are not limited to, buffers etc.

The present invention also relates to an immunodetection kit comprising antibodies specific for all, or a unique portion, of the polypeptide encoded in PSGGB (such as antibodies specific for the peptide of the present invention) and reagents to effect formation of and detection of polypeptide:antibody or peptide:antibody complex. The antibodies included in the kit may be monoclonal, monospecific or polyclonal antibodies. The kit can be used to detect the presence of the polypeptide in tissue samples or preferably, biological fluid samples.

EXAMPLES

The following non-limiting Examples are given to aid in understanding the present invention.

Sequence of PSG95

Three PS$\beta$G cDNAs, PSG16, PSG93, and PSG95, have been isolated and characterized in the laboratory of the present inventor (Watanabe, S. and Chou, J. Y., 1988, *J. Biol. Chem.* 263:2049-2054; Watanabe, S. and Chou, J. Y., 1988, in *Placental and Endometrial Proteins*, ed. Mizutani, S., VNU Science Press, Japan, pp. 155-158). Sequence analysis indicates that PSG16 and PSG93 are highly similar, and that PSG93 contains an additional 86 base pairs beginning at nucleotide 1309 of PSG16 (Watanabe, S. and Chou, J. Y., 1988, *J. Biol. Chem.* 263:2049-2054). Moreover, PSG93 is identical to cDNAs PSGD (Streydio, C., Lacka, K., Swillens, S. and Vassart, G., 1988, *Biochem. Biophys. Res. Commun.* 154:130-137), hPSP11 (Chan, W. -Y., Borjigin, J., Zheng, Q. -X. and Shupert, W. L., 1988, *DNA* 7:545-555), FL-NCA-2 (Khan, W. N. and Hammarstrom, S., 1989, *Biochem. Biophys. Res. Commun.* 161:525-535), PSG1a (Zimmermann, W., Weiss, M. and Thompson, J. A., 1989, *Biochem. Biophys. Res. Commun.* 163:1197-1209) and PS$\beta$G81 (Niemann, S. C., Flake, A., Bohn, H. and Bartels, I., 1989, *Hum. Genet.* 82:239-243) isolated from several other laboratories, suggesting that PSG93 represents the major PS$\beta$G species. Like PSG93, the PSG95 encoded protein contains a 34 amino acid leader peptide, an N-A1-A2-B2-C domain arrangement, seven potential glycosylation sites, and six invariant cysteine residues which are important in disulfide bond formation (FIG. 1). Sequence analysis of cDNA PSG95 indicates that it is similar to PSGC, PSG1d, and FL-NCA, but is larger than all of them. The 5' sequences of these four cDNAs are identical, except that PSG95 contains the longest 5'-untranslated region. The coding regions of PSG95, PSG1d, and FL-NCA are identical and encode a protein of 426 amino acids. However, PSG95 contains an additional 518 and 523 bp in the 3'-untranslated region as compared to PSG1d and FL-NCA, respectively. PSGC is identical to PSG95 from nucleotides 45 to 1404 of PSG95; however, PSGC lacks nucleotides 1405 to 1759 of PSG95. Homology between these two cDNAs again resumes from nucleotide 1760 to the 3' end of PSG95. Because of the 355 base pair insertion in PSG95, the proteins encoded by PSG95 and PSGC differ in their sequences at the carboxyl termini. The 3'-end divergence may be generated by alternative splicing events, as discussed later. A complete analysis of the sequences of PSG95 compared to PSG93 and PSG16 reveals that PSG95 and PSG93 are identical until the alternative splicing junction in the carboxyl terminus, at nucleotide 1404 of PSG95 (FIG. 1). However, PSG95 and PSG93 differ from PSG16 at nucleotides 215, 287, 288, 764, as well as 3' to the alternative splice point (Watanabe, S. and Chou, J. Y., 1988, *J. Biol. Chem.* 263:2049-2054). Thus, PSG16 represents a polymorphic variant.

Library Screening and Characterization of cDNA and Genomic Clones

To identify a novel genomic PS$\beta$G clone, a human placental cDNA library in $\lambda$gt11 (Dr. Frank Gonzalez, National Institutes of Health) was screened with a probe containing the 5' EcoRI-BamHI fragment of the PS$\beta$G cDNA clone PSG16 (Watanabe, S. and Chou, J. Y., 1988, *J. Biol. Chem.* 263, 2049-2054) and a human leukocyte genomic library in EMBL-3 (Clontech Laboratories, Inc., Palo Alto, Calif.) was screened with a probe containing the entire PSG16 cDNA sequence. The cDNA and genomic inserts from positive clones were subcloned into pUC or pGEM vectors (Promega Biotech, Madison, Wis.) for further characterization. Sequencing of cDNA and genomic clones was accomplished by the Sanger dideoxy chain-termination method (Sanger, F., Nicklen, S. and Coulson, A. R., 1977, *Proc. Natl. Acad. Sci. U.S.A.* 74, 5463-5467) using [$\alpha$-$^{35}$S] dATP (400 Ci/mmol; Amersham Corp., Arlington Heights, Ill.). Both strands of the cDNA and genomic clones were sequences as a means to identify intron-exon junctions.

Nineteen PS$\beta$G genomic clones which strongly hybridized with a probe containing the entire PSG16 cDNA were isolated. These genomic clones were characterized by their restriction endonuclease digestion patterns and by their abilities to hybridize with PS$\beta$G-specific probes. Clone A, which hybridized strongly with a probe specific to the 5' end of PSG93 (nucleotides 1-142) and contained a restriction endonuclease pattern similar to that of human genomic DNA was extensively analyzed.

A careful analysis of clone A indicates that it contains two linked PS$\beta$G genes which are arranged in the same 5' to 3' orientation (FIG. 2). The upstream gene, PSGGA, contains the A2 and B-C exons in its 3, region. The A2 exon is composed of 279 bp encoding 93 amino acids which is 98% similar to the A2 protein domain of PSG16/PSG93/PSG95 at the nucleotide level and 95% similar at the amino acid level. The 3' exon, designated B-C, contains 1950 bp and four alternative splicing points within the carboxyl terminus, and encodes the PS$\beta$G B2 protein domain and the 3'-untranslated regions of mRNAs similar to PSG16, PSG93, PSG95, and PSGC. These appear to have been generated by alternative splicing events. The majority of PS$\beta$G mRNAs, which differ in their 3' region, diverge precisely at splice site 1 (designated C1 in FIG. 2). The PSGGA sequences immediately following this point share 92% sequence similarity with PSG95 and contain the entire 3' region of the PSG95-like sequence from nucleotide 1405 to the 3' end of PSG95. PSG1d (Zimmermann, W., Weiss, M. and Thompson, J. A., 1989, *Biochem. Biophys. Res. Commun.* 163, 1197-1209) and FL-NCA (Khan, W. N., Osterman, A. and Hammarstrom, S., 1989, *Proc. Natl. Acad. Sci. U.S.A.* 86, 3332-3336) are identical to PSG95, except that the FL-NCA-like sequence ends just after splice 2, designated C2 in FIG. 2 and utilize a polyadenylation site beginning at PSGGA nucleotide 902. PSGC (Streydio, C., Lacka, K., Swillens, S. and Vassart, G., 1988, *Biochem. Biophys. Res. Commun.* 154, 130–137) and PSG95 differ by the presence of an additional 355 bp sequence (nucleotide 1405–1759) in PSG95 (FIG. 1). In PSGGA, this PSG95-like sequence appears to be an intron in the generation of a PSGC-like mRNA. This sequence contains the consensus splicing site GT-AG (Breathnach, R. Benoist, C., O'Hare, K., and Chambon, P., 1978, *Proc. Natl. Acad Sci. U.S.A.* 75, 4853–4857). Within PSGGA, the PSGC-like 3' terminus begins at nucleotide 889 (C2 in FIG. 2). The single polyadenylation site shared by the putative PSG95- and PSGC-like transcripts begins at PSGGA nucleotide 1409.

Fifty bases downstream from the ends of the PSG95- and PSGC-like sequences is another junction, designated splice site C3. This 50 bp sequence does not contain the intron consensus splicing site GT-AG; thus it may represent the true 3' end of the PSG95- and PSGC-like transcripts. Beginning at splice site C3, the PSGGA sequence shares 94% sequence similarity with the 3' region of PSG93. The present inventor previously reported that PSG93 differs from PSG16 by the presence of an additional 86 bp beginning at nucleotide 1309 of PSG16 (Watanabe, S. and Chou, J. Y., 1988, *J. Biol. Chem.* 263, 2049–2054). Splice site C3 marks the beginning of this 86-bp insert and, thus, nucleotides 535–1482 (which contain the C1 and C2 sequences and the consensus splicing site GT-AG), act as an intron to generate a PSG93-like mRNA. The 86-bp region of the PSG93-like sequence is designated as C3 (FIG. 2) and begins at PSGGA nucleotide 1483. Immediately following the 86-bp sequence is splice site C4 which represents where the PSG16-like message joins after splicing at site C1. Sequences in C4 share 94% similarity with the shared 3' sequences of PSG16 and PSG93. The shared polyadenylation site for the putative PSG93- and PSG16-like messages begins at nucleotide 2152 of PSGGA. Although similarity exists between PSGGA and previously reported PSβG cDNAs, PSGGA is not identical to any of them.

The nucleotide sequence of the downstream gene, PSGGB is identical to cDNA PSG6 reported by Zimmermann et al. (Zimmermann, W., Weiss, M. and Thompson, J. A., 1989, *Biochem. Biophys. Res. Commun.* 163, 1197–1209). Approximately 180 bp of the PSGGB sequence upstream from the transcriptional start site of the PSG93-like sequence (the beginning of exon 5'/L) was obtained. The 5'/L exon (approximately 250 bp in length) encodes the 5' untranslated region and the first 21 amino acids of the leader peptide. The L/N exon (363 bp in length) encodes the remaining leader codon and the N protein domain (108 amino acid residues). Amino acid residues 126–128 of pSGGB are arginine-glycine-asparagine. This tripeptide is known to be the signal surface active component of cellular adhesion molecules (Cunningham, B. A., Hemperly, J. J., Murray, B. A., Predoger, E. A., Brackenbury, R. and Edelman, G. M., 1987, *Science* 236, 799–806), and gives a possible clue to the function of this member of the PSβG family.

Recently, two other PSβG genomic fragments were isolated (Oikawa, S., Inuzuka, C., Kosaki, G. and Nakazato, H., 1988, *Biochem. Biophys. Res. Commun.* 156, 68–77; Oikawa, S., Inuzuka, C., Kuroki, M., Matsuoka, Y., Kosaki, G. and Nakazato, H., 1989, *Biochem. Biophys. Res. Commun.* 142, 1021–1031). The gene fragment CGM35 (Oikawa, S., Inuzuka, C., Kosaki, G. and Nakazato, H., 1988, *Biochem. Biophys. Res. Commun.* 156, 68–77) contains the A1, B1, A2 and B-C exons. The B-C exon also contains several splice points, and alternative splicing is likely in this gene fragment as a means to generate different mRNA species; however, CGM35 does not encode any of the reported PSβG mRNAs. The second gene fragment, PSG-HL 12-2 (Oikawa, S., Inuzuka, C., Kuroki, M., Matsuoka, Y., Kosaki, G. and Nakazato, H., 1989, *Biochem. Biophys. Res. Commun.* 142, 1021–1031), contains the 5'/L, L/N, A1, B1, and A2 exons with part of the B2 domain of the B-C exon. A PSβG cDNA (PSβG-HL-clone 22) has been identified which has the N-A2-B2-C domain arrangement and shares complete sequence homology with genomic fragment PSG-HL 12-2 (Oikawa, S., Inuzuka, C., Kuroki, M., Matsuoka, Y., Kosaki, G. and Nakazato, H., 1989, *Biochem. Biophys. Res. Commun.* 142, 1021–1031). This suggests that the A1 and B1 exons have been spliced out to generate this mRNA. A comparison of the intron sequences of PSGGA and PSGGB with the corresponding intron sequences of PSG-HL 12-2 reveals that they are very similar. The similarity in intron sequences between the different PSβG genes indicates that divergence within this family is a relatively recent evolutionary event.

Although a putative CAAT box is located at nucleotides 118–123 of PSGGB, there is no consensus TATA box-like sequence in the 5'-flanking region of this gene. The linkage of PSGGA and PSGGB indicates that an additional 5' exon does not exist in PSGGB. This is supported by previous primer extension experiments which showed that PSG93 may be a full-length cDNA clone (Watanabe, S. and Chou, J. Y., 1988, *J. Biol. Chem.* 263, 2049–2054), and the entire 5'-untranslated region of PSG93 is represented in PSGGB.

Oligonucleotide Probes

Oligonucleotide probes were synthesized from areas of the PSGGA and PSGGB sequences which contain deletions or substitutions as deduced from comparisons with cDNAs PSG93/PSG95 using the Cyclone Plus DNA Synthesizer (Milligen Biosearch, Navato, Calif.). Oligonucleotide (Oligo) 1 is a 30-mer containing nucleotides 619–648 of PSGGB. Oligos 2 and 3 contain nucleotides 45–68 and 323–355 of PSGGA, respectively. Oligo 4 is a 66-mer containing nucleotides 1240–1305 of PSG6, a transcript encoded by PSGGB. PSG6 was previously described by Zimmermann et al. [*Biochem. Biophys. Res. Commun.* 163, 1197–1209, 1989]. Oligonucleotides were labeled at the 5'-OH end with [α-$^{32}$P] ATP using T4 polynucleotide kinase (Bethesda Research Laboratories, Gaithersburg, Md.).

FIG. 2 illustrates the nucleotide sequences of PSGGA and PSGGB and the proposed exon and protein sequences compared to PSG16, PSG93, PSG95, and PSGC. To demonstrate that mRNAs encoded by PSGGA and PSGGB are actually expressed in placental tissue, four oligonucleotide probes (oligo 1, 2, 3 and 4) that would hybridize to the PSGGA and PSGGB sequences in areas which contain deletions or substitutions as compared with cDNA PSG93/PSG95 were synthesized. Oligo 1 (30-mer) is located in the N domain of PSGGB and includes the triple bp deletion present in this region as well as four bp substitutions when compared with PSG95/PSG93. Oligo 2 (24-mer) is located in the A2 domain of PSGGA where it contains 3 single bp substitutions when compared with PSG95/PSG93.

Oligo 3 (33-mer) is located in the B2 domain of PSGGA where it contains four single bp substitutions and one double bp substitution when compared with PSG95/PSG93.

Trophoblastic Tissues

Human term placenta was obtained from normal pregnancy. Three hydatidiform mole tissue specimens were obtained from the University of Colorado Health Sciences Center, Denver, Colo. Samples 1 and 2 were non-invasive moles and sample 3 was an invasive mole.

Nucleic Acid Hybridization Analysis

Total RNA was extracted by the guanidinium thiocyanate method of Chirgwin et al. (Chirgwin, J. M., Przybyla, A. E., MacDonald, R. J. and Rutter, W. J., 1979, *Biochemistry* 18, 5294-5299), and poly(A)+ RNA was obtained by oligo (dT)-cellulose chromatography. RNA was separated by electrophoresis on 1.2% agarose gels containing 2.2M formaldehyde (Lehrach, H., Diamond, D., Wozney, J. M. and Boedtker, H., 1977, *Biochemistry* 16, 4743-4751), and transferred to Zetabind membranes by electroblotting. The filters were hybridized at 50° C. in the presence of an oligo probe ($3 \times 10^6$ cpm/ml) in a previously described buffer (Watanabe, S. and Chou, J. Y., 1988, *J. Biol. Chem.* 263, 2049-2054) from which dextran sulfate was removed. The blots were washed two times in 2x SSC containing 0.1% SDS for 30 min. at room temperature, then three times in 0.2 ×SSC containing 0.1% SDS for 30 min. at 50° C.

The Northern blots shown in FIG. 3 reveal that the PSGGB-specific probe, oligo 1, hybridized with a major 1.7-kb mRNA and a minor 1.5-kb mRNA in the three molar tissues, but with a 2.0-kb mRNA (major) and a 1.5-kb mRNA in term placental tissue. Moreover, the oligo 1 hybridizable transcript appears to be preferentially expressed in hydatidiform mole when compared to normal trophoblastic tissue (FIG. 3). Furthermore, the level of the transcript that hybridized with oligo 1 was higher in an invasive mole when compared with two non-invasive moles. The PSGGB specific oligo 4 was also specific for molar tissue and initials results indicated it is more specific than oligo 1.

The PSGGA probe, oligo 2, is the least specific probe and hybridized with two mRNAs of 2.2- and 1.5-kb in term placenta, and a 1.7-kb message in molar tissue. However, the relative amounts of oligo 2 hybridizable message were higher in placenta than in hydatidiform moles. Oligo 3, which is more specific to PSGGA, hybridized poorly with either placenta or molar RNA.

For purposes of completing the background description and present disclosure, each of the published articles, patents and patent applications heretofore identified in this specification is hereby incorporated by reference into the specification.

The foregoing invention has been described in some detail for purposes of clarity and understanding. It will also be obvious that various combinations in form and detail can be made without departing from the scope of the invention.

What is claimed is:

1. A DNA or RNA probe consisting essentially of the following nucleotide sequence: the sense strands 5'-CACGGTCAAATTATATATGGGCCTGCCTAC-3' or 5'-GAGACAGCATCTCCCCAGGTTACCTATGCTGGTCCAAACACCTGGTTTC AAGAAATCCTTCTGCTG-3' or the antisense strands 5'-GTAGGCAGGCCCATATATAATTTGACCGTG-3' or 5'-CAGCAGAAGGATTTCTTGAAACCAGGTGTTTGGACCAGCATAGGTAACC TGGGGAGATGCTGTCTC-3'.

2. A peptide encoded in the sense sequence of claim 1 and having one of the following amino acid sequences: N terminus-His Gly Gln Ile Ile Tyr Gly Pro Ala Tyr-C terminus or N terminus-Glu Thr Ala Ser Pro Gln Val Thr Tyr Ala Gly Pro Asn Thr Trp Phe Gln Glu Ile Leu Leu Leu-C terminus.

3. An antibody specific for a peptide of claim 3 and encoded by the PSGGB pregnancy-specific beta$_1$-glycoprotein mRNA that is preferentially expressed in human hydatidiform molar trophoblastic tissue.

4. An antibody specific for the peptide encoded by a nucleotide sequence of claim 2 wherein the peptide comprises at least 6 amino acids of the PSGGB pregnancy-specific beta$_1$-glycoprotein that is preferentially expressed in human hydatidiform molar trophoblastic tissue.

5. The antibody according to claim 4 which is polyclonal.

6. The antibody according to claim 4 which is monoclonal.

7. The antibody according to claim 4 which is monospecific.

8. A bioassay for detection of a gestational trophoblastic disease comprising the steps of:
   a) contacting a tissue sample with a probe of claim 2 specific for PSGGB mRNA expressed in human hydatidiform molar trophoblastic tissue, under conditions such that regions of messenger RNA (mRNA) in said tissue sample and said probe with complementary sequences will base pair so that a RNA:probe complex is formed; and
   b) detecting the presence or absence of said RNA:-probe complex.

9. The bioassay according to claim 8 wherein said probe is a DNA probe.

10. The bioassay according to claim 8 wherein said probe is an RNA probe.

11. The bioassay according to claim 8 wherein said disease is hydatidiform mole, invasive mole or choriocarcinoma.

12. The bioassay according to claim 8 wherein said disease is hydatidiform mole.

13. The bioassay according to claim 8 wherein said tissue is tumor biopsies, placental and endometrium and myometrium tissues, fetal tissues, fetal sera, maternal sera, amnion tissues or amniotic fluids.

14. A bioassay for detection of a gestational trophoblastic disease comprising the steps of:
   a) contacting a tissue sample with the antibody of claim 4 or claim 5 under conditions such that said antibody can form a complex with said polypeptide in said tissue sample; and
   b) detecting the presence or absence of said antibody:polypeptide or antibody:peptide complex.

15. The bioassay according to claim 14 wherein said disease is hydatidiform mole, invasive mole or choriocarcinoma.

16. The bioassay according to claim 14 wherein said disease is hydatidiform mole.

17. The bioassay according to claim 14 wherein said tissue is tumor biopsies, placental and endometrium and myometrium tissues, fetal tissues, fetal sera, maternal sera, amnion tissues or amniotic fluids.

18. A diagnostic kit comprising a DNA or RNA probe specific for PSSGB and reagents to effect formation of and detection of an RNA:DNA or RNA:RNA complex wherein said probe has the following sequence: the sense strands 5'-CACGGTCAAAT-TATATATGGGCCTGCCTAC-3' or 5'-GAGACAGCATCTCCCCAGGTTACC-TATGCTGGTCCAAACACCTGGTTTC AA-GAAATCCTTCTGCTG-3' or the antisense strands 5'-GTAGGCAGGCCCATATATAATTT-GACCGTG-3' or 5'-CAGCAGAAGGATTTCTT-GAAACCAGGTGTTTGGACCAGCATAGG-TAACC TGGGGAGATGCTGTCTC-3'.

19. An immunodetection kit comprising antibodies of claim 4 or 5 specific for all, or a segment of at least 6 amino acids of the polypeptide encoded by the PSGGB pregnancy-specific beta$_1$-glycoprotein mRNA that is preferentially expressed in human hydatidiform molar trophoblastic tissue and reagents to effect formation of and detection of polypeptide:antibody or peptide:antibody complex.

* * * * *